United States Patent [19]
Müller et al.

[11] Patent Number: 5,365,032
[45] Date of Patent: Nov. 15, 1994

[54] METHOD OF CUTTING BY MEANS OF LASER RADIATION

[75] Inventors: Gerhard J. Müller, Berlin; Gerfried Giebel, Homburg/Saar, both of Germany

[73] Assignee: Optec Gesellschaft fur optische Technik mbH, Burbach, Germany

[21] Appl. No.: 8,793

[22] Filed: Jan. 25, 1993

[30] Foreign Application Priority Data

Jan. 27, 1992 [DE] Germany ............... 4202487

[51] Int. Cl.⁵ ............................................ B23K 26/06
[52] U.S. Cl. ................... 219/121.67; 219/121.72; 219/121.75; 219/121.77
[58] Field of Search .............. 219/124.67, 121.72, 219/121.77, 121.61, 121.71, 121.75

[56] References Cited

U.S. PATENT DOCUMENTS

| | | | |
|---|---|---|---|
| 4,273,398 | 6/1981 | Summers et al. | 219/121.67 X |
| 4,468,551 | 8/1984 | Neiheisel | 219/121.75 X |
| 4,713,518 | 12/1987 | Yamazaki et al. | 219/121.69 |
| 5,055,653 | 10/1991 | Funami et al. | 219/121.75 |
| 5,103,074 | 4/1992 | Watanabe et al. | 219/121.68 |

FOREIGN PATENT DOCUMENTS

| | | |
|---|---|---|
| 1565144 | 2/1970 | Germany . |
| 3340112 | 6/1984 | Germany . |
| 9113803 | 3/1992 | Germany . |
| 59-87424 | 9/1984 | Japan . |
| 63-177982 | 11/1988 | Japan . |

*Primary Examiner*—C. L. Albritton
*Attorney, Agent, or Firm*—Spencer, Frank & Schneider

[57] ABSTRACT

A method of cutting by means of laser radiation wherein, particularly in order to increase the cutting efficiency in connection with composite materials, the laser radiation focused along a line extending transversely to the direction of radiation.

18 Claims, 5 Drawing Sheets

FIG. 5
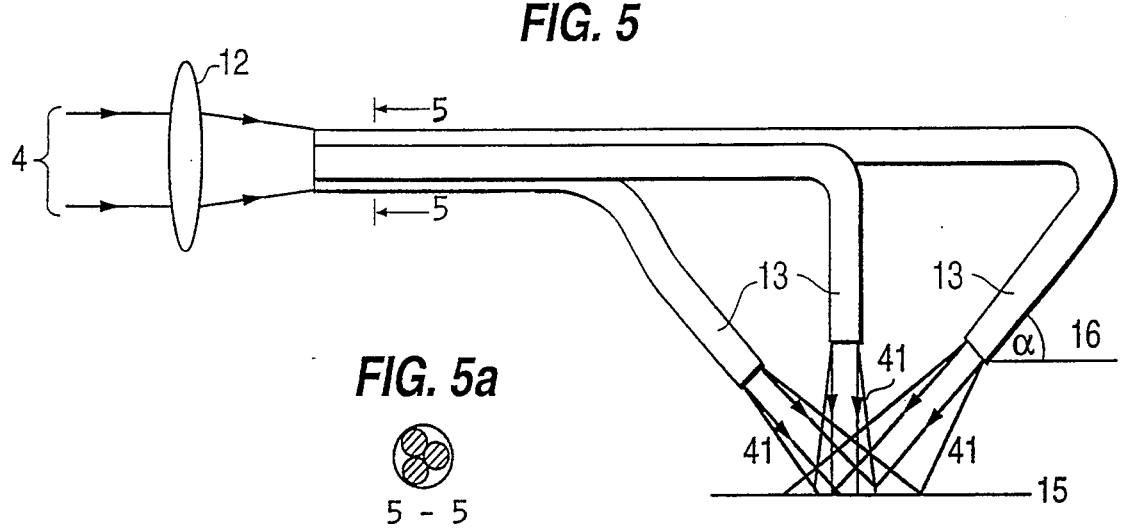
FIG. 5a
5 — 5
FIG. 5b
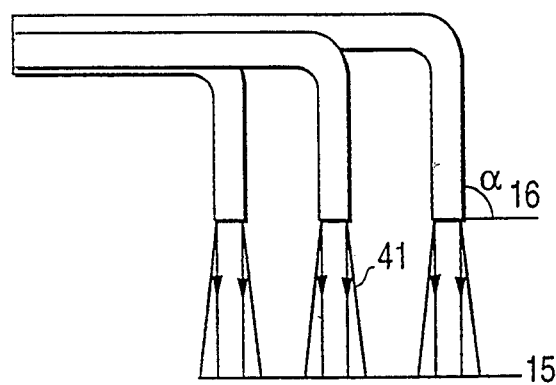

METHOD OF CUTTING BY MEANS OF LASER RADIATION

BACKGROUND OF THE INVENTION

The invention relates to a method of cutting by means of laser radiation and to a device for implementing the method.

In connection with materials processing, it is known to conduct laser radiation—emanating from a laser generator—by way of beam guidance systems to the location of interaction and to there focus it, if required, by means of optical imaging elements in order to increase the power or energy density.

In that case, the cross section of the focus generally corresponds to a reduced image of the beam waist of the laser radiation in the resonator. In practice, this image is approximately point shaped. Prior art radiation guidance systems are configured either as articulated multiple-mirror arms or as light waveguides. Most of the light waveguides, particularly those operating in the ultraviolet or infrared range, still exhibit technical deficiencies with respect to the transmission of higher energy or power densities so that the desired energy or power values, which must lie sufficiently high above the starting threshold of the respective process, cannot be transmitted reliably.

When lasers operating in a spectral range from 150 nm to 11 μm are employed for cutting structured materials which pose different resistances to the cutting laser beam—here called "composite materials"—and particularly insofar as hard organic tissue is concerned, there exists the additional problem that the focused beam, as a result of the respective texture, cuts to greatly differing depths—with respect to the same action periods.

German Unexamined Published Patent Application No. 1,565,144 discloses, for materials processing by means of laser radiation, to shape the laser beam with cylindrical lenses in order to drill rectangular holes.

SUMMARY OF THE INVENTION

It is the object of the invention to provide a method and an appropriate apparatus of the above-mentioned type with which the cutting characteristics can be homogenized while overcoming the above-mentioned drawbacks and improving energy utilization of the laser radiation.

The above and other objects are accomplished according to the invention by the provision of an anamorphic optical system for focusing laser radiation along a focal line extending transversely to the direction of the radiation; and adjusting means for adjusting the length of the focal line and the degree of focusing along the focal line. Typically, the anamorphic optical system includes a cylindrical lens.

In one embodiment, a linear lens array follows the cylindrical lens and is oriented parallel to the focal line for resolving the focal line into individual focal points.

In an alternative embodiment, the anamorphic optical system has an optical axis in the direction of the laser radiation. A cylindrical lens is provided that is located on the optical axis. Additionally, the adjusting means includes means for rotating the cylindrical lens about the optical axis.

In yet a third embodiment, the adjusting means includes a plurality of individual light waveguides for transmitting the laser radiation. The individual light waveguides have distal ends and are aligned so that the distal ends of the light waveguides are inclined along a straight line, so that a distribution of radiation components supplied to the individual light waveguides is derived by amplitude or wavefront division.

The invention includes the realization that the orientation of the laser radiation along a line—particularly with the use of an anamorphic optical system—and the thus formed line of interactions between laser radiation and material surface to be worked results in averaging in such a way that, as long as the laser radiation remains within or exceeds the necessary (minimum) threshold energy or threshold power density, instabilities of the laser radiation as well as inhomogeneities of the (composite) material can be averaged out in a favorable manner. By focusing the laser radiation along a line (and possibly providing for corresponding guidance along this line in the manner of a scalpel), regions of different material resistance come (successively) in contact with regions of different radiation intensity so that a higher cutting power can be realized. The increased amplitude of the local and temporal power fluctuations compared to unfocused radiation is here better adapted to the fluctuation range of the different local changes in the material properties so that the removal of material is more uniform.

In particular, the successive application of laser energy along a line during manipulation of the instrument in a manner corresponding to a cutting (back and forth) movement results in the superposition of the effect realized by the individual radiation components along the line. The configuration of the laser bundle in the manner of a cutting edge resulted in great effectiveness during material removal with great local energy density without the total amount of heat generated reaching unduly high values.

As an advantageous modification of the inventive concept, a second anamorphic component is employed in a device for implementing the method according to the invention in addition to the above-mentioned component but so that it is rotatable about the optical axis relative to the first-mentioned component. Thus the length of the interaction line can be set as desired within wide limits as a function of the displacement angle, which is significant particularly if the cutting direction is changed along small radii.

In an advantageous modification of the device according to the invention for implementing precision cuts it is provided to derive a signal that is proportional to the displacement angle of the anamorphic optical system so as to change with the aid of that signal the output power or energy of the laser in such a manner that the power (energy) density in the interaction zone always corresponds to a desired, preset value.

In another preferred embodiment, a linear lens array is connected to the output of the first-mentioned anamorphic component so as to resolve the focal line into individual focal points along a line. This is employed particularly if a further increase of the energy (power) density is considered in order to exceed the required process thresholds.

In another advantageous modification of the inventive concept, the task at hand can also be accomplished with fiber-optic components. In that case, the laser radiation generated by known means is coupled by means of amplitude or wavefront division into several individual fibers. Toward their distal ends, these individual fibers then take on a configuration that is oriented in the manner of a line in one plane.

In this variation of the invention, the length of the line of the useful laser radiation can be set by changing the inclination of the end regions of the fibers relative to one another.

The laser radiation focused along a line by means of the laser cutting device according to the invention can be guided to the interaction zone in a particularly favorable manner by means of an articulated multiple-mirror arm. An anamorphic optical system employed for focusing is preferably composed of a cylindrical lens. The laser radiation employed for the laser cutting device according to the invention has a wavelength, in particular, between 150 nm and 11 μm. The variable pulse lengths are at least 10 ns.

The shortening of the linear focus of the laser radiation can be varied by providing a further cylindrical lens that can be rotated on the same optical axis.

A position sensor connected with the lens mount provides a signal that is proportional to the rotation angle and can be utilized to regulate the power or energy density.

In an alternative embodiment of the invention, the laser radiation is transmitted by means of light waveguides. These preferably have their distal ends arranged in a line in one plane and are mounted in such a way that the respective beam bundle illuminates the line-shaped region with variable convergence.

BRIEF DESCRIPTION OF THE DRAWINGS

Other advantageous modifications of the invention are disclosed in the dependent claims and will now be described in greater detail together with a description of the preferred embodiment of the invention and with reference to the drawing figures, in which:

FIGS. 5 to 5b depict a variation of the embodiment of FIG. 4 including various detail views;

DETAILED DESCRIPTION OF THE PREFERRED EMBODIMENTS

Figure 1:
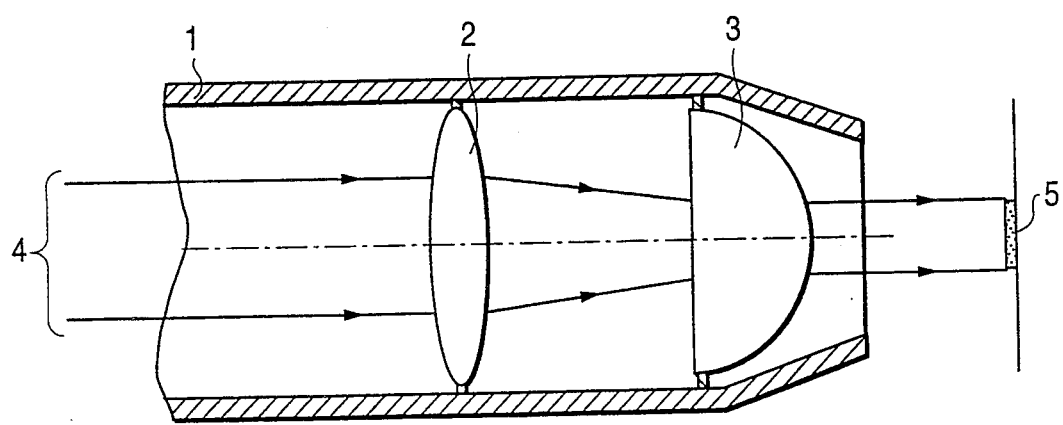
FIG. 1 is a partial sectional view of a first embodiment of a device for implementing the method according to the invention.

In the embodiment of the invention illustrated in FIG. 1, a bundle of laser beams 4 travels from a handheld member 1 of which only its distal region is shown, through a focusing lens 2 to a cylindrical lens 3 which constitutes the anamorphic optical system. The cylindrical lens focuses the radiation in the direction toward the composite material to be cut in such a manner that the radiation receives a rectangular to linear profile when seen in cross section. With this device, materials, particularly those having an inhomogeneous structure, can be worked according to the method of the invention so that a considerable increase in cutting efficiency can be realized for composite materials. The beam bundle is preferably moved back and forth relative to the object to be cut in the direction toward the largest radiation cross section in the way a scalpel is guided so that different parts of the radiation cross section come successively into interaction with regions of the material to be cut that are stationary relative to it. This causes local inhomogeneities of the material as well as those of the laser radiation to be averaged out so that, on the average, a uniform cutting effect is realized.

The laser radiation at the distal end of a (non-illustrated) articulated mirror arm enables the bundle of laser beams to be concentrated onto a focal line in such a way that, upon exceeding the threshold energy (power) density, the laser radiation goes into interaction with the material along an interaction line and thus it is possible to average out very well any point-to-point instabilities of the laser radiation with corresponding point-to-point inhomogeneities of the composite material.

In a further embodiment of the invention—shown in FIG. 2—the components bearing the same reference numerals correspond in their function to those described in connection with FIG. 1. In addition to the first anamorphic component in the form of cylindrical lens 3, a further anamorphic component 6 is provided which is additionally rotatable about the optical axis (shown in dash-dot lines). Thus the length of the interaction line can be adjusted at will within wide limits as a function of the displacement angle, which is particularly significant if the cutting direction is changed over small radii. If the device according to the invention is employed for the performance of precision cuts, a signal is derived according to the invention which is proportional to the displacement angle of the anamorphic optical system and with which the output power or energy of the laser can be changed in such a way that the power (energy) density in the interaction zone always corresponds to a preset value.

Figure 3:
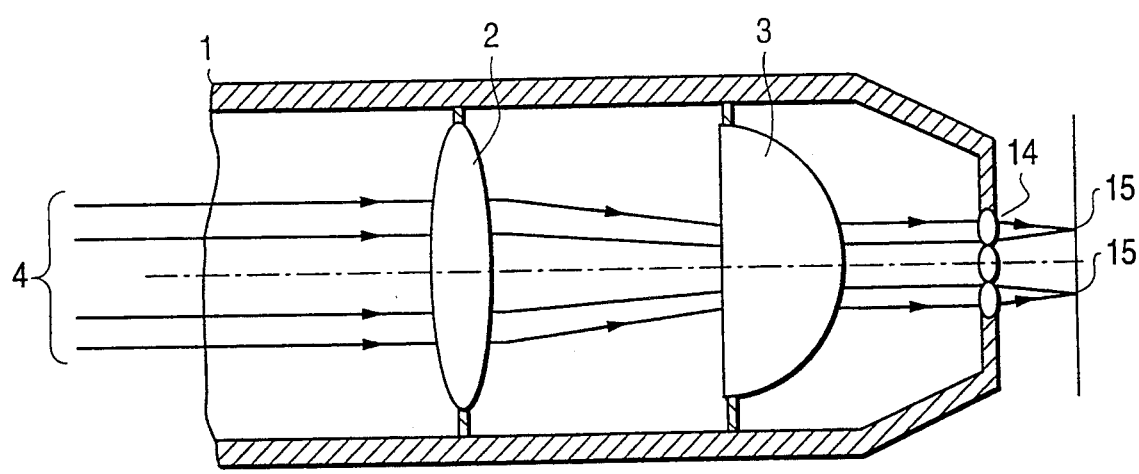
FIG. 3 depicts another variation of the embodiment of FIG. 1 including additional lenses for focusing along a line.

In another preferred embodiment of the invention shown in FIG. 3—in which the arrangement corresponds to that of FIG. 1, with corresponding reference numerals being employed—the first-mentioned anamorphic component 3 is followed in the optical beam path by a linear lens array 14 that serves to resolve the focal line into individual focal points along a line. In this way it is possible to further concentrate the energy in a linear region if this should become necessary to further increase the energy (power) density when the required process thresholds are exceeded. This is applicable particularly under the aspect of making available radiation ranges of different energy content for the treatment of inhomogeneous material layers.

Figure 4:
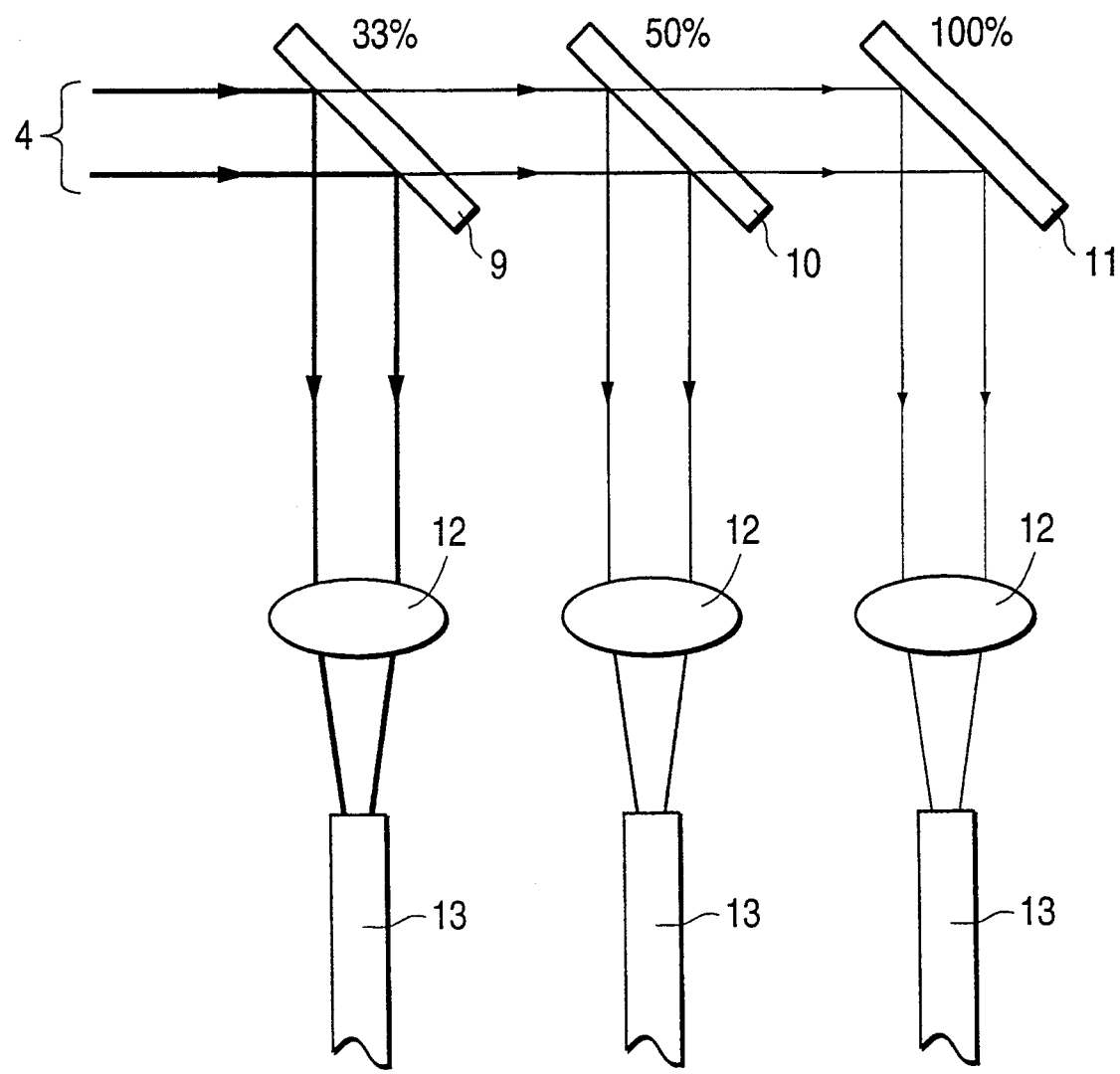
FIG. 4 depicts a further embodiment according to the invention, including a distribution of the incident laser radiation to a plurality of light conductors.

In a further embodiment of the invention as illustrated in two variations in FIGS. 4 and 5, fiber-optic components are employed to accomplish the task and produce a linear extent of the radiation cross section. To this extent, the embodiment corresponds to that of FIG. 1 in which a cylindrical lens is employed for the corresponding purpose.

In the embodiment according to FIG. 4, the incident laser radiation is distributed by means of amplitude division through deflection mirrors 9 to 11 and intermediately connected focusing lenses 12 to individual optical fibers 13 which conduct the thus divided laser radiation to the distal (application) end of the arrangement.

In this embodiment as well, a variation of the dimensions of the linear cross section can be realized by means of a rotatable cylindrical lens which should be disposed at the distal output end in a linear cross-sectional region of the fibers.

In the embodiment variation according to FIG. 5, the laser radiation incident through a common focusing lens 12 is directed by wavefront division into a plurality of individual fibers 13 that are combined into a bundle. The cross section of FIG. 5 is shown separately in FIG. 5a and shows the bundled arrangement of the individual fibers for the purpose of conducting the radiation concentrated by focusing lens 12 as completely as possible into the individual fibers.

In FIG. 5b, the individual fibers are shown with their end regions in parallel orientation. The laser radiation impinges perpendicularly on material surface 15. The angle $\alpha$ enclosed between a line 16 that is parallel to the surface of the material and the direction of the fibers is 90°. The distal ends of these individual fibers are arranged in parallel in one plane.

Figure 6A:
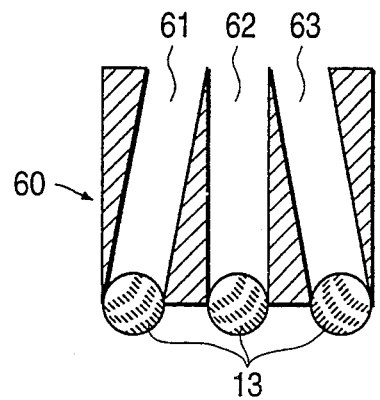
FIGS. 6a an 6b depict further details of embodiments according to FIG. 4 or 5 for changing the inclination of the optical fibers relative to one another.
Figure 6B:
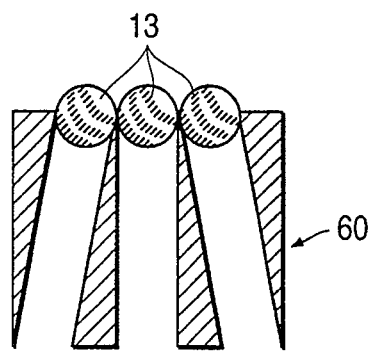

According to a further feature, the length of the line can be changed by adjusting the inclination of the fibers relative to one another. In a preferred embodiment shown in two positions in FIGS. 6a and 6b, the length of the expanse of the beam bundles transverse to the direction of the beam can be set by means of a comb-like device 60 which acts on the optical fibers, shown in cross section, by means of diverging guides 61 to 63. In the position shown in FIG. 6a, the optical conductors are at their greatest distance, while in the position according to FIG. 6b, they are close together so that the length of the transverse extent of the laser bundle is reduced. The optical fibers are here pivotally fastened, in particular, at some distance from the comb-like device so that their relative inclination can be varied.

Figure 2:
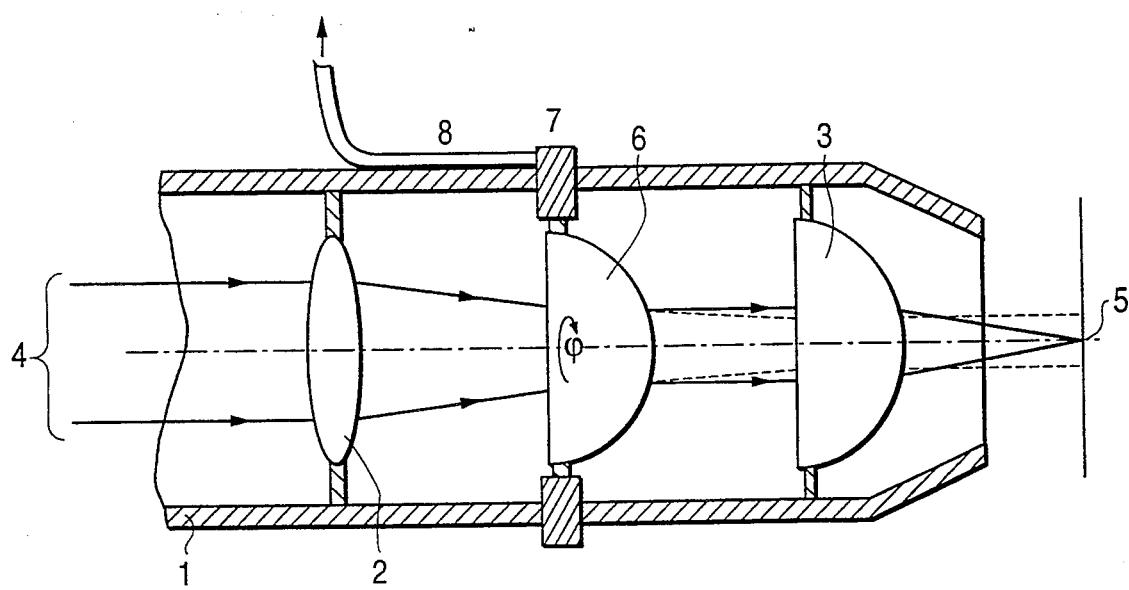
FIG. 2 depicts a variation of the embodiment of FIG. 1 which includes a further rotatable cylindrical lens.
Figure 7:
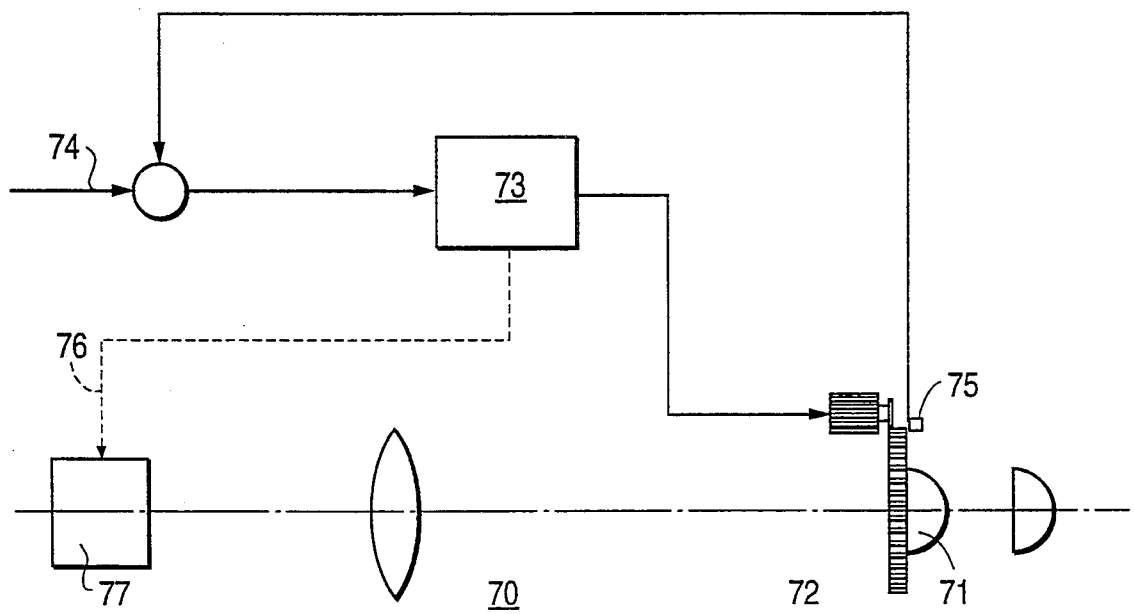
FIG. 7 depicts a device for changing the length of the linear cross section of the laser beam bundle produced by one of the embodiments of the invention illustrated above.

In an embodiment shown in FIG. 7, a circuit is provided for automatically adjusting the radiation energy in the application range for an arrangement of the type shown in FIG. 2. In a radiation arrangement 70, the second cylindrical lens 71 can be rotated by means of a mechanical drive activated by a control circuit 73. By means of a predetermined desired value 74, it is thus possible to set the length of the radiation cross section. A position sensor 75 and a corresponding return loop permits the position of cylindrical lens 71 to be accurately reproduced.

By way of a further connection 76, shown in dashed lines, to laser source 77, it is further possible, by influencing the duration of the energy pulses, to additionally influence the energy density in the application area—and thus overall within wide limits.

If the realizable radiation energy lies below the desired set value, the energy density at the object is increased by adjustment of the cylindrical lens in the direction of shortening the length of the line transversely to the radiation direction. In the other case, the adjustment is made in the opposite direction. In this way, the optimum energy value can be determined empirically for different materials and can be given by way of external settings.

Due to the regulating effect, the respective value is also maintained within a wide range even if there are instabilities in the incoming radiation. In addition (as already mentioned and indicated by the dashed line arrows) the pulse duration can also be varied as a further value for influencing the laser energy at the application object. Greater pulse durations then contribute to an increase in the emitted energy.

The invention is not limited in its embodiments to the above-described preferred embodiment. Rather, a number of variations are conceivable which take advantage of the described solution even for basically different configurations.

We claim:

1. A device for cutting material with laser radiation, comprising:
   an anamorphic optical system including at least one cylindrical lens, said anamorphic optical system for focusing laser radiation along a focal line extending transversely to the direction of the radiation;
   a linear lens array following said cylinder lens and being oriented parallel to the focal line for resolving the focal line into individual focal points; and
   adjusting means for adjusting the length of the focal line and the degree of focusing along the focal line.

2. A device for cutting material with laser radiation, comprising:
   an anamorphic optical system for focusing laser radiation along a focal line extending transversely to the direction of the radiation, said anamorphic optical system including a plurality of individual light waveguides for transmitting the laser radiation, said individual light waveguides having distal ends and being aligned so that the distal ends of said light waveguides are inclined along a straight line, wherein a distribution of radiation components supplied to the individual light waveguides is derived by amplitude or wavefront division; and
   adjusting means for adjusting the length of the focal line and the degree of focusing along the focal line.

3. A device according to claim 2, said anamorphic optical system further includes at least one cylindrical lens.

4. A device for cutting material with laser radiation, comprising:
   an anamorphic optical system having an optical axis in the direction of the laser radiation and at least one cylindrical lens located on the optical axis, said anamorphic optical system for focusing laser radiation along a focal line extending transversely to the direction of the radiation; and
   adjusting means comprising a rotatable cylindrical lens and means for rotating said rotatable cylindrical lens about the optical axis for adjusting the length of the focal line and the degree of focusing along the focal line.

5. A device according to claim 4, wherein said means for rotating includes a rotatable holder which holds said rotatable cylindrical lens.

6. A device according to claim 5, wherein said means for adjusting comprises a position sensor located at said rotatable holder for sensing position of said rotatable holder and putting out an angle dependent signal that is a function of the angular orientation of the focal line.

7. A device according to one of claim 5, wherein said holder comprises a lens mount for said rotatable cylindrical lens.

8. A device according to claim 6, wherein said adjusting means further comprises a control device for influencing the energy density of the laser radiation as a function of the angle dependent signal.

9. A device according to claim 8, wherein said control device controls the energy density of the laser radiation to remain essentially constant, independent of the length of the focal line.

10. A device according to claim 1, wherein the laser radiation has a wavelength essentially between 150 nm and 11 μm.

11. A device according to claim 1, wherein the pulse duration of the laser radiation is at least 10 ns.

12. A device according to claim 2, wherein the laser radiation has a wavelength essentially between 150 nm and 11 μm.

13. A device according to claim 2, wherein the pulse duration of the laser radiation is at least 10 ns 14. A device according to claim 4, wherein the laser radiation has a wavelength essentially between 150 nm and 11 μm.

15. A device according to claim 4, wherein the pulse duration of the laser radiation is at least 10 ns.

16. A device according to claim 2, wherein said adjusting means comprises means for adjusting the inclination of the distal ends of the light waveguides in the direction of the focal line for concentrating or dispersing the laser radiation.

17. A device according to claim 16, wherein said means for adjusting the inclination comprises a comb-like structure having diverging guides for holding the distal ends of the respective individual light waveguides, the inclination of the individual light waveguides being adjusted by sliding said comb-like structure in a direction transverse to said individual light.

18. A device according to claim 17, wherein the individual light waveguides are fastened together at a sufficient distance from the comb-like structure to permit pivoting of the individual light waveguides relative to one another.

* * * * *